United States Patent
Calleja et al.

(10) Patent No.: US 10,597,630 B2
(45) Date of Patent: Mar. 24, 2020

(54) METHOD FOR CULTURE OF MICROALGAE (71) Applicant: FERMENTALG, Libourne (FR)

(72) Inventors: Pierre Calleja, Libourne (FR); Cyril Rols, Perigueux (FR); Julien Pagliardini, Bordeaux (FR); Brice Bourdenx, Merignac (FR)

(73) Assignee: FERMENTALG, Libourne (FR)

( * ) Notice: Subject to any disclaimer, the term of this patent is extended or adjusted under 35 U.S.C. 154(b) by 251 days.

(21) Appl. No.: 15/506,377

(22) PCT Filed: Aug. 26, 2015

(86) PCT No.: PCT/FR2015/052274
§ 371 (c)(1),
(2) Date: Feb. 24, 2017

(87) PCT Pub. No.: WO2016/030631
PCT Pub. Date: Mar. 3, 2016

(65) Prior Publication Data
US 2017/0247654 A1    Aug. 31, 2017

(30) Foreign Application Priority Data

Aug. 27, 2014  (FR) ..................... 14 58025

(51) Int. Cl.
*C12N 1/12* (2006.01)
*C12P 7/64* (2006.01)

(52) U.S. Cl.
CPC ............. *C12N 1/12* (2013.01); *C12P 7/6427* (2013.01)

(58) Field of Classification Search
None
See application file for complete search history.

(56) References Cited

U.S. PATENT DOCUMENTS

2008/0032352 A1* 2/2008 Behrens ................ A61K 36/02
435/134
2016/0145668 A1* 5/2016 Garnier .................. C12P 23/00
435/67

FOREIGN PATENT DOCUMENTS

| EP | 0 622 463 A2 | 11/1994 |
|---|---|---|
| EP | 0 657 543 A1 | 6/1995 |
| EP | 2 194 138 A1 | 6/2010 |
| ES | 2 333 571 A1 | 2/2010 |
| JP | H09-65871 A | 3/1997 |
| WO | 2001/04338 A1 | 1/2001 |
| WO | 2005/035775 A1 | 4/2005 |
| WO | 2014/074770 A2 | 5/2014 |

OTHER PUBLICATIONS

Mendes et al., Crypthecodinium cohnii with emphasis on DHA production: a review, J. Appl. Phycol., Published Online Aug. 17, 2008, pp. 199-214, vol. 21.
De Swaaf et al., High-Cell-Density Fed-Batch Cultivation of the Docosahexaenoic Acid Producing Marine Alga Crypthecodinium cohnii, Biotechnology and Bioengineering, Mar. 20, 2003, pp. 666-672, vol. 81, No. 6.
Provasoli et al., The Development of Artificial Media for Marine Algae, Arch. Mikrobiol., 1957, pp. 392-428, vol. 25.
Prabowo et al., Diversity of *Crypthecodinium* spp. (Dinophyceae) From Okinawa Prefecture, Japan, Journal of Marine Science and Technology, 2013, pp. 181-191, vol. 21, Suppl.
Bligh et al., A Rapid Method of Total Lipid Extraction and Purification, Canadian Journal of Biochemistry and Physiology, Aug. 1959, pp. 911-917, vol. 37, No. 8.
Folch et al., A Simple Method for the Isolation and Purification of Total Lipides from Animal Tissues, J. Biol. Chem., May 1957, pp. 497-509, vol. 226, No. 1.
Jiang et al., Effects of salinity on cell growth and docosahexaenoic acid content of the heterotrophic marine rnicroalga Crypthecodinium cohnii, Journal of Industrial Microbiology, 1999, pp. 508-513, vol. 23, No. 6.
Bumbak et al., Best practices in heterotrophic high-cell-density microalgal processes: achievements, potential and possible limitations, Appl Microbiol Biotechnol, Published online May 13, 2011, pp. 31-46, vol. 91, No. 1.
Yaguchi et al., Production of High Yields of Docosahexaenoic Acid by *Schizochytrium* sp. Strain SR21, JACOS, 1997, pp. 1431-1434, vol. 74, No. 11.
Martins et al., Alternative Sources of n-3 Long-Chain Polyunsaturated Fatty Acids in Marine Microalgae, Marine Drugs, 2013, pp. 2259-2281, vol. 11, No. 7.
Chaung et al., Effect of culture conditions on growth, lipid content, and fatty acid composition of Aurantiochytrium rnangrovei strain BL10, AMB Express, 2012, p. 42, vol. 2, No. 1.
Coelho et al., High Cell Density Cultures of Microalgae under Fed-batch and Continuous Growth, Chemical Engineering Transactions, 2014, pp. 313-318, vol. 38.
International Search Report, dated Nov. 6, 2015, from corresponding PCT application.
Excerpt from Nerad TA, ATCC Medium: 460 A2E6 Medium, American type culture collection, catalogue of protists, 1993, 18th edn. Rockville, USA.

* cited by examiner

*Primary Examiner* — Vera Afremova
(74) *Attorney, Agent, or Firm* — Young & Thompson (57) ABSTRACT

Disclosed is a method for culture of microalgae, advantageously of the genus *Crypthecodinium* having a gene coding for the small 18s ribosomal RNA subunit having a genetic similarity of at least 96% with the same gene of the strain of the species *Crypthecodinium cohnii* deposited in the CCAP (Culture Collection of Algae and Protozoa) under number CCAP 1104/3 in a defined chemical medium.

22 Claims, 5 Drawing Sheets

METHOD FOR CULTURE OF MICROALGAE

The invention relates to a method for culturing microalgae having a gene encoding the small subunit 18s ribosomal RNA having a genetic similarity of at least 96% with the same gene of the strain of the species *Crypthecodinium cohnii* deposited in the CCAP (Culture Collection of Algae and Protozoa, SAMS Ltd., Scottish Marine Institute, Oban, Argyll PA37 1QA Scotland) under number CCAP 1104/3, also called in the present text "CCAP strain 1104/3".

Advantageously, the method according to the invention concerns microalgae strains of the genus *Crypthecodinium* having a gene encoding the small subunit 18s ribosomal RNA having a genetic similarity of at least 96% with the same gene of the strain of the species *Crypthecodinium cohnii* deposited in the CCAP (Culture Collection of Algae and Protozoa) under number CCAP 1104/3.

In the present text, the expression "microalgae concerned by the invention" should be understood to indicate microalgae, advantageously microalgae of the genus *Cryptheco- dinium*, having a gene encoding the small subunit 18s ribosomal RNA having a genetic similarity of at least 96% with the same gene of the strain of the species *Cryptheco- dinium cohnii* deposited in the CCAP (Culture Collection of Algae and Protozoa) under number CCAP 1104/3.

Similarly, by "strain" is meant not only the natural microalgae strains concerned by the invention, but also the mutants of said natural strains. By "mutants" is meant an organism derived from the original strain, the genetic inheritance of which has been modified either by a natural process or by physicochemical methods known to the person skilled in the art, who can generate random mutations (UV, etc.), i.e., by genetic engineering methods.

By "chemically defined culture medium" is meant a culture medium wherein the content of each element is known. Precisely, the invention concerns a medium not comprising rich or complex organic matter such as, for example, yeast extracts or other complex sources of proteins or other organic matter, such as peptone or other rich inorganic matter such as, for example, inorganic sea salts or other complex growth agents, not having a fixed concentration of each of their components.

By "high cell density" is meant a biomass concentration in the culture medium at least equal to 50 g/L, even greater.

More precisely, the invention concerns a method for culturing said microalgae concerned by the invention in a chemically defined medium that can enable high-density production of said microalgae strains concerned by the invention.

The method according to the invention can further make it possible to obtain a high biomass density and an enrichment in the lipid and more particularly the docosahexaenoic acid (DHEA) content of said microalgae concerned by the invention thus cultivated.

Among polyunsaturated fatty acids (PUFAs), certain highly unsaturated fatty acids of the omega-3 series (ω3-PUFA), in particular eicosapentaenoic acid (EPA or ω3 C20:5) and docosahexaenoic acid (DHEA or ω3 C22:6), and of the omega-6 series (ω6-PUFA), particularly arachidonic acid (ARA or AA or eicosatetraenoic acid or ω6 C20:4), have a recognized nutritional importance and a high potential in terms of therapeutic applications.

Regarded as an essential nutrient, DHEA is necessary to the normal and functional development of cells and plays a crucial role in various biochemical processes and functions. It is essential to the development of the central nervous system and to retinal function, by incorporation in cell membranes, and plays a key role in the acquisition and the satisfactory maintenance of the mechanisms involved in vision and memory. DHEA is also used in the composition of pharmaceutical products, either as an active ingredient, as a vector for active ingredients or as a precursor. By "precursor" is meant a molecule from which it is possible to synthesize other molecules that are more or less complex than said precursor.

In the case of a pharmaceutical use of DHEA, it is necessary to provide a molecule in its pure state. It is for example necessary to reduce to a minimum contamination by docosapentaenoic acid (DPA) or eicosapentaenoic acid (EPA). The latter two molecules are often produced with DHEA in microalgae. To facilitate this purification, to obtain, if possible easily, a product having a purity in conformity with the regulatory requirements applicable to food products or to pharmaceutical products, and at lower cost, it is desirable to start with an oil wherein DHEA is the major PUFA and wherein the contents of molecules such as EPA or DPA are very low.

The DHEA currently used in the pharmaceutical industry and in foodstuffs is chiefly obtained from fish oil.

The use of DHEA obtained from microalgae oil, for example derived from bioreactor cultures, can make it possible to avoid the contamination problems of the oils typically used, for example fish oils, potentially contaminated by pollutants like heavy metals, pesticides and polychlorobiphenyls (PCB), as well as problems of odor and of lack of oxidative stability that these oils may have, etc.

Microalgae are currently the subject of many industrial projects because certain species are capable of accumulating or secreting large amounts of lipids, particularly polyunsaturated fatty acids.

Microalgae of the genus *Crypthecodinium* are known for their ability to produce an oil rich in DHEA and containing low contents of DPA, EPA and other PUFAs [Mendes A, et al. (2008) *Crypthecodinium cohnii* with emphasis on DHEA production: a review. J. Appl. Phycol., 21:199-214]. The DHEA contained in this oil is thus easier to purify compared, for example, to the DHEA contained in oil from Thraustochytrids of the *Aurantiochytrium* or *Schizochytrium* type or to the DHEA contained in fish oil.

The oil produced from microalgae concerned by the invention is thus particularly suitable for producing DHEA for pharmaceutical and nutraceutical applications, and for use in the form of DHEA esters, for example ethyl esters.

To implement the industrial-scale production of fatty acids by microalgae, several factors must be taken into account to make the production profitable. Among these factors, mention may be made of:

- the costs of raw materials and equipment (the purchase or lease and the maintenance thereof), as well as of labor;
- the technical demands of the production: for example, the number and technical difficulty of the preculture and culture steps, the on-line monitoring of the cultures, and the steps for treating the biomass derived from the culture to add value to the product;
- the quality, reproducibility and yield of the products derived from the culture;
- the treatment of effluents generated by the culture.

The culture media commonly used currently in the prior art to cultivate microalgae concerned by the invention, in heterotrophic or mixotrophic conditions, contain significant amounts of rich organic matter, also called complex organic matter. By "rich" or "complex" organic matter is meant unpurified organic matter appearing in the form of mixtures for which the exact composition and the concentrations of the various components of the mixture are not known with precision, are not controlled, and may vary significantly from one batch to another. As examples of rich or complex organic matter, mention may be made of yeast extracts or peptones that are products of a protein hydrolysis reaction.

These media may also contain rich inorganic matter (also called complex salts), i.e., unpurified inorganic matter appearing in the form of mixtures the concentrations and the exact composition of which may vary significantly from one batch to another, and are not controlled. By way of example, mention may be made of sea salts.

To simplify matters, the expression "complex medium" will be used in the present text to indicate a culture medium comprising rich or complex organic matter or rich or complex inorganic matter or both.

Several publications describe high cell density production of DHEA in complex medium with microalgae strains concerned by the invention.

De Swaaf M E, et al. [(2003) High-cell-density fed-batch cultivation of the docosahexaenoic acid producing marine alga *Cryptecodinium cohnii*. Biotechnol Bioeng. 81:666-672 doi:10.1002/bit.10513] describe for example the following complex medium: 10 g/L yeast extract; 25 g/L sea salt; 8 g/L carbon source, said carbon source being sodium acetate. The authors describe production in fed-batch fermentation mode of 109 g/L biomass (dry matter) that is rich in lipids (61%), themselves consisting of 31% DHEA. The maximum productivity obtained under these conditions is 38 mg DHEA per liter of medium per hour. On the other hand, the authors describe that the problem of culture viscosity linked to secretion of a polysaccharide by the microalga would prevent the culture from being carrying out on an industrial scale.

WO 2001/004338 describes a method for culturing *Crypthecodinium cohnii* using acetic acid as the principal carbon source in a complex culture medium comprising yeast extracts and sea salts. This method makes it possible to reach 45 g/L biomass, including 12.3 g/L lipids, in 140 h, with a 31% DHEA content in the lipids.

EP 0622463 describes a continuous culture process for *Crypthecodinium cohnii* in complex medium comprising glucose and yeast extract, respectively, as principal carbon source and as nitrogen source. In fed-batch mode, productivities of biomass (dry matter) of 0.21 g/L/h and of DHEA of 0.01 g/L/h are described.

However, the use of complex media for culturing microalgae concerned by the invention, in processes for producing oil and/or other molecules of interest, presents the following disadvantages:

- it involves additional costs in terms of downstream processing (DSP) of the biomass to arrive at the final product,
- it does not make it possible to fully control the composition of the culture medium, and thus the reproducibility of the culture process, from one batch of raw materials to another,
- it limits the ability to characterize the composition of the complex medium and thus limits the traceability of the product,
- it leads to additional costs compared to the use of chemically defined media. Indeed, yeast extract-type media are more expensive than an inorganic nitrogen, minerals, vitamins-type mixture.

The use of complex media to reach high cell densities also leads to accumulation in the culture medium of substances not used by the microalgae, such as minerals, proteins, substances that inhibit microalgae growth (organic acids, etc.), etc. Indeed, complex media are usually not fully consumed by the microalgae, which are content to take the elements necessary to their needs. The unused fraction accumulates in the culture medium. This can have disadvantages, particularly in the case of high cell density processes, in downstream processing steps such as, for example, biomass drying steps and in purification steps such as, for example, ultrafiltration steps.

The use of complex media the exact composition of which is not known presents a further disadvantage for the process. Indeed, their organic nitrogen, mineral or vitamin content can have an influence on the metabolism of the microalgae, and thus on their growth and their production of molecules of interest.

The exact composition of these raw materials not being guaranteed, it is likely to vary by the supplier, by the exact product number and even from one batch to another. The reproducibility of the composition of the desired final product may then vary from one batch to another. This thus represents an obstacle in terms of standardizing the final products derived from the biomass obtained by culture in complex medium.

Lastly, as the exact composition of the complex media is not fully known, the possibilities of product traceability and quality control are reduced. However, product traceability and quality control are important, even essential, particularly when a pharmaceutical application of said product is envisaged.

Similarly, in a general manner, the complex media used currently in the prior art to cultivate microalgae concerned by the invention, in heterotrophic or mixotrophic conditions, may also contain significant quantities of sea salt, the composition of which is not standardized and thus varies by the supplier, by the product number, and even from one batch to another. This can also make it difficult to reproduce the culture method with undefined culture media.

The massive use of sodium chloride (NaCl) for culturing microalgae in methods for producing oil and/or other molecules of interest further leads to substantial additional costs in terms of investment and of liquid waste processing and limits the ability to add value to the by-products. Indeed, chloride ions can cause a degradation of culture devices such as, for example, the stainless steel used in said culture devices. This has as a consequence either the use of particular alloys that are more resistant to chloride ions, but are more expensive, or an early degradation of the production equipment. In both cases, investment costs are substantially higher.

Furthermore, the massive use of sodium chloride (or other sodium salts, particularly sodium sulfate and sodium carbonate) leads to substantial additional costs in terms of liquid waste processing, particularly water desalination.

Lastly, the excess presence of sodium salts in the oil cake-type by-products constituted by the biomass remaining after oil extraction can make it difficult to add value to them, in particular for animal feed.

Replacing these salts by a mixture of known minerals, derived from purified minerals, allows better control of the process and better traceability of the raw materials.

This replacing of salts, particularly of sea salt, by a known mixture may also make it possible to substantially reduce the quantity of NaCl present in the medium potentially to adjust it to the strict needs of the strain and thus to reduce problems related to the presence of sodium chloride (NaCl) in the medium.

The formulation of chemically defined media for culturing microalgae strains concerned by the invention has been described on several occasions in the literature. In 1957, Provasoli and Gold published the first so-called "synthetic" medium for a *Crypthecodinium cohnii* strain [Provasoli, L., J. J. A. McLaughlin and M. R. Droop: The development of artificial media for marine algae. Arch. Mikrobiol. 25, 392-428 (1957)].

Since that date, other groups have also published on the subject. In 1993, Nerad reported the creation of $A_2E_6$ medium, notably used today to preserve strain collections (ATCC 460) [Nerad T A (1993) American type culture collection, catalogue of protists, $18^{th}$ Ed. Rockville, USA ATCC Medium: 460 A2E6 Medium], the recipe of which is available on the ATCC website.

More recently, US 2008/0032352 A1 described a heterotrophic culture method with a chemically defined medium directed particularly at reducing the concentration of chloride ions.

However, in the prior art describing the growth of microalgae strains concerned by the invention, in synthetic medium, the authors do not succeed in reaching high cell densities. The biomass concentrations obtained are lower than 50 g dry matter per liter of medium.

Thus, these media described in the prior art seem more suited to maintenance of the strain than to production with high biomass concentrations (greater than 50 g/L), and thus do not seem suited to industrialization of the method.

There is thus still a need to provide synthetic culture media, the composition of which is well defined and well controlled, that are reproducible and that make it possible to reach high cell densities.

It is desirable to be able to cultivate microalgae strains concerned by the invention, without using complex media, under optimal conditions to maximize the yield of the fatty acid to be produced, while reducing fermentation production costs, by facilitating downstream processing, by improving the control of the process and the reproducibility thereof and by improving traceability and quality control throughout the value chain.

This is particularly important in the context of a pharmaceutical application, where quality control of the raw materials and reproducibility of the method are critical parameters, while controlling the medium and the method make it possible to obtain an oil highly concentrated in DHEA, which facilitates the purification steps.

In particular, it is desirable to provide methods for culturing microalgae strains concerned by the invention, which make it possible to substantially reduce, even eliminate, the use of complex media and particularly sea salts.

In the context of the present invention, it is desirable to obtain biomass and lipid densities sufficient for industrial DHEA production. It may thus be desirable to obtain concentrations, for example, greater than 50 g/L dry matter, preferably greater than 150 g/L and more preferentially greater than 200 g/L dry matter.

It may be desirable not only to be able to produce a high cell density, but also DHEA quantities sufficient for industrial-scale DHEA production. It may also be desirable to obtain proportions of other PUFAs, such as DPA, at least lower than 5%, preferably at least lower than 2%, more preferably at least lower than 1%, even more preferentially lower than 0.8%, advantageously at least lower than 0.5%, or at least lower than 0.1%, most advantageously preferably at least lower than 0.01%.

These are a few of the objectives which the Applicant has set forth and which the present invention aims to achieve.

Thus, the Applicant has developed a chemically defined medium, adapted to high cell density culture of microalgae strains concerned by the invention. The method developed can in particular make it possible to reach a biomass concentration equivalent to or greater than those described in the prior art in complex medium, while preserving competitive productivity in relation to the latter cultures.

The use of a chemically defined medium according to the invention can in particular make it possible to control the quantity of each element present in the medium.

Thus, by using this chemically defined medium, the inventors developed a new method for high cell density culture of microalgae concerned by the invention.

Moreover, according to a particular embodiment of the invention, the culture method can make it possible to direct the metabolism of the strains toward improved DHEA production. This can be accomplished by controlling the supplies of nutrients, and particularly the supplies of carbon, nitrogen and phosphate source. By this method, the inventors succeeded in increasing by at least 30%, even up to more than 50%, the DHEA content in the lipids produced by microalgae strains concerned by the invention, compared to culture in complex medium, while maintaining the concentration of other PUFAs at a low value, advantageously at least lower than 5%, more advantageously lower than 1%, preferentially at least lower than 0.8%.

The oil thus produced by the method of the invention can be highly enriched in DHEA, which constitutes a significant improvement compared to the methods of the prior art.

Furthermore, the costs associated with downstream processing are reduced in relation to the methods of the prior art.

Thus, the Applicant succeeded in developing a chemically defined culture medium, i.e., generally without rich or complex media and without rich or complex inorganic matter, particularly without sea salts.

The medium according to the invention can make it possible to cultivate microalgae strains concerned by the invention, and can make it possible to obtain a high-density biomass production of said microalgae that can, for example, be at least greater than 50 g/L, preferably than 100 g/L, 150 g/L, 200 g/L or 250 g/L, more preferentially 270 g/L dry matter.

The DHEA levels in the culture prepared according to the method according to the invention can be for example at least greater than 5 g/L or 10 g/L, preferably greater than 20 g/L, and more preferentially greater than 30 g/L, while maintaining the production of other PUFAs at for example less than 1% of the total fatty acid content, preferentially less than 0.8% of the total fatty acid content.

The invention thus relates to microalgae strains, advantageously microalgae strains of the genus *Crypthecodinium*, having a gene encoding the small subunit 18s ribosomal RNA having a genetic similarity of at least 96% with the same gene of the strain of the species *Crypthecodinium cohnii* deposited in the CCAP (Culture Collection of Algae and Protozoa) under number CCAP 1104/3.

The reference strain, *Crypthecodinium cohnii* deposited in the CCAP (Culture Collection of Algae and Protozoa) under number CCAP 1104/3, belongs to Clade 2 as described in the article: [Prabowo D A, Hiraishi O, and Suda S. DIVERSITY OF *Crypthecodinium* spp. (DINOPHYCEAE) FROM OKINAWA PREFECTURE, JAPAN. Journal of Marine Science and Technology, Vol. 21, Suppl., pp. 181-191 (2013)].

As non-limiting examples it is possible to cite as microalgae concerned by the invention the strains of the species *Crypthecodinium* sp. D31, *Crypthecodinium* sp. SS2-2, *Crypthecodinium* sp. SZ13-3, *Crypthecodinium* sp. SZ13-2, *Crypthecodinium* sp. SZ13-1, *Crypthecodinium cohnii*

(GenBank accession number: M64245), *Crypthecodinium cohnii* (GenBank accession number: FJ821501), *Cryptheco­dinium* sp. OKI5-1, *Crypthecodinium* sp. SZ7-1, *Crypthecodinium* sp. ISG40-1, *Crypthecodinium* sp. ISK1-2, *Crypthecodinium* sp. ISK1-1, *Crypthecodinium cohnii* (GenBank accession number: DQ241737) or the strains deposited by the Applicant in the CCAP, *Crypthecodinium cohnii* deposited under number CCAP 1104/3, *Crypthecodinium cohnii* deposited under number CCAP 1104/5 or *Crypthecodinium cohnii* deposited under number CCAP 1104/4.

Table 1 below presents the percent similarity of the genes encoding the small subunit 18s ribosomal RNA of various strains having a genetic similarity of at least 96% with the same gene of the strain of the species *Crypthecodinium cohnii* deposited in the CCAP (Culture Collection of Algae and Protozoa) under number CCAP 1104/3, of the strains mentioned above.

TABLE 1

| Strains | GenBank accession number of the compared sequence | Length of the compared sequences (%) | % similarity with the reference |
|---|---|---|---|
| *Crypthecodinium* sp. D31 | AB811790 | 100% | 99% |
| *Crypthecodinium* sp. SS2-2 | AB871552 | 98% | 99% |
| *Crypthecodinium* sp. SZ13-3 | AB871549 | 98% | 99% |
| *Crypthecodinium* sp. SZ13-2 | AB871548 | 98% | 99% |
| *Crypthecodinium* sp. SZ13-1 | AB871547 | 98% | 99% |
| *Crypthecodinium cohnii* | M64245 | 100% | 99% |
| *Crypthecodinium cohnii* | FJ821501 | 100% | 99% |
| *Crypthecodinium* sp. OKI5-1 | AB871551 | 98% | 99% |
| *Crypthecodinium* sp. SZ7-1 | AB871550 | 98% | 99% |
| *Crypthecodinium* sp. ISG40-1 | AB871546 | 98% | 99% |
| *Crypthecodinium* sp. SK1-2 | AB871545 | 98% | 99% |
| *Crypthecodinium* sp. SK1-1 | AB871544 | 98% | 99% |
| *Crypthecodinium cohnii* | DQ241737 | 91% | 96% |

The present invention thus relates to a method for culturing microalgae strains concerned by the invention, in heterotrophic or mixotrophic conditions, in a chemically defined medium. This culture method makes it possible to obtain high densities of biomass, of lipids, and specifically of DHEA, while maintaining a low DPA content.

Microalgae strains concerned by the invention are able to grow in a chemically defined culture medium developed by the Applicant.

The invention thus relates to a chemically defined microalgae culture medium that can comprise at least macroelements, microelements and vitamins to which a carbon source is added.

More precisely, the culture medium according to the invention can comprise as macroelements, in addition to the carbon source, sodium chloride (NaCl), magnesium chloride, advantageously in hexahydrate form ($MgCl_2$ $6H_2O$), sodium bicarbonate ($N_aHCO_3$), potassium hydrogen phosphate ($K_2HPO_4$), calcium chloride, advantageously in dihydrate form ($CaCl_2$ $2H_2O$), iron (III) chloride ($FeCl_3$ $6H_2O$), boric acid ($H_3BO_3$) and a nitrogen source that can be a nitrate salt such as, for example, potassium nitrate ($KNO_3$), sodium nitrate ($NaNO_3$), calcium nitrate ($Ca(NO_3)_2$) or a glutamate salt or an ammonium salt or urea.

According to the invention, sodium chloride can be at a concentration between 2 and 8 g/L, preferentially between 4 and 6 g/L.

According to the invention, potassium hydrogen phosphate can be at a concentration between 0.3 and 0.7 g/L, preferentially between 0.4 and 0.6 g/L.

According to the invention, magnesium chloride can be at a concentration between 0.6 and 1.4 g/L, advantageously between 0.8 and 1.2 g/L.

According to the invention, sodium bicarbonate can be at a concentration between 0.14 and 0.26 g/L, advantageously between 0.16 and 0.24 g/L.

According to the invention, the nitrogen source can be at a concentration between 1.7 and 3.1 g/L, advantageously between 1.9 and 2.9 g/L.

According to the invention, calcium chloride can be at a concentration between 1.4 and 2.6 g/L, advantageously between 1.6 and 2.4 g/L.

According to the invention, iron (III) chloride can be at a concentration between 0.016 and 0.024 g/L, advantageously between 0.018 and 0.022 g/L.

According to the invention, boric acid can be at a concentration between 0.046 and 0.74 g/L, advantageously between 0.048 and 0.72 g/L.

Similarly, the culture medium according to the invention can comprise as microelements disodium ethylenediaminetetraacetic acid ($Na_2EDTA$), manganese (II) chloride tetrahydrate ($MnCl_2$ $4H_2O$), zinc chloride ($ZnCl_2$), cobalt chloride hexahydrate ($CoCl_2$ $6H_2O$), copper sulfate pentahydrate ($CuSO_4$ $5H_2O$), and nickel sulfate hexahydrate ($NiSO_4$ $6H_2O$).

According to the invention, disodium ethylenediaminetetraacetic acid can be at a concentration between 0.01 and 0.08 g/L, advantageously between 0.015 and 0.06 g/L.

According to the invention, manganese (II) chloride tetrahydrate can be at a concentration between 0.001 and 0.02 g/L, advantageously between 0.002 and 0.01 g/L.

According to the invention, zinc chloride can be at a concentration between 0.0001 and 0.0008 g/L, advantageously between 0.00015 and 0.0006 g/L.

According to the invention, cobalt chloride hexahydrate can be at a concentration between 0.00005 and 0.0005 g/L, advantageously between 0.00007 and 0.0003 g/L.

According to the invention, copper sulfate pentahydrate can be at a concentration between 0.00007 and 0.004 g/L, advantageously between 0.0009 and 0.0036 g/L.

According to the invention, nickel sulfate hexahydrate can be at a concentration between 0.0005 and 0.003 g/L advantageously between 0.0007 and 0.0028 g/L.

Similarly, the culture medium according to the invention can comprise as vitamins biotin, thiamin, cobalamin or vitamin B12 and pantothenate or vitamin B5.

According to the invention, biotin can be at a concentration between $0.5 \times 16^{-6}$ and $1.5 \times 10^{-4}$ g/L, advantageously between $1 \times 10^{-6}$ and $1 \times 10^{-4}$ g/L.

According to the invention, thiamin can be at a concentration between $0.5 \times 16^{-6}$ and $1.5 \times 10^{-4}$ g/L, advantageously between $1 \times 10^{-6}$ and $1 \times 10^{-4}$ g/L.

According to the invention, cobalamin can be at a concentration between $0.5 \times 16^{-6}$ and $1.5 \times 10^{-4}$ g/L, advantageously between $1 \times 10^{-6}$ and $1 \times 10^{-4}$ g/L.

According to the invention, pantothenate can be at a concentration between $0.5 \times 16^{-6}$ and $1.5 \times 10^{-4}$ g/L, advantageously between $1 \times 10^{-6}$ and $1 \times 10^{-4}$ g/L.

According to the invention, the defined culture medium can comprise a carbon source. Exemplary carbon sources usable in the defined medium according to the invention can be one (or more) carbohydrate(s), one (or more) acetate(s), one or more alcohols or one or more complex molecules. Advantageously, the carbon source can be a mixture of carbon sources. For example, products derived from the biotransformation of starch, for example from wheat, from corn or from potato, in particular starch hydrolysates, which consist of small molecules, constitute carbon substrates usable according to the invention.

As examples of carbohydrates usable in the defined medium according to the invention, mention may be made of saccharose (or sucrose), lactose, starch, amylose, amylopectin, cellulose or derivatives thereof, glycogen, dihydroxyacetone, glyceraldehyde, erythrose, threose, erythrulose, ribose, ribofuranose, arabinose, xylose, lyxose, ribulose, xylulose, allose, altrose, glucose, glucopyranose, mannose, gulose, idose, galactose, galactopyranose, talose, psicose, fructose, fructofuranose, sorbose, tagatose, sedoheptulose, 2-deoxyribofuranose, trehalose, maltose, cellobiose, isomaltose, raffinose, gentianose, agar-agar, hyaluronic acid, ortho-nitrophenyl-β-D-galactopyranoside (ONPG).

As an example of acetate mention may be made of sodium acetate or acetic acid.

As an example of alcohol mention may be made of ethanol or glycerol.

Preferentially according to the invention, the carbon source can be glycerol.

According to the invention, the concentration of the carbon source can be between 10 mM and 500 mM. However, the person skilled in the art will be able to adapt the concentration of the carbon source according to its nature and according to the needs of the strain cultivated. For example, glucose, glycerol and ethanol can have a concentration between 200 and 500 mM. If the carbon source is acetate, for example sodium acetate or acetic acid, the concentrations thereof in the culture medium according to the invention can be between 10 and 100 mM.

According to a variant of the invention, the chemically defined medium can consist of only the elements described above to which is added a carbon source as previously described.

The invention also relates to a method for culturing microalgae strains, advantageously microalgae of the genus *Crypthecodinium*, having a gene encoding the small subunit 18s ribosomal RNA having a genetic similarity of at least 96% with the same gene of the strain of the species *Crypthecodinium cohnii* deposited in the CCAP (Culture Collection of Algae and Protozoa) under number CCAP 1104/3, characterized in that it can comprise at least a first step wherein said strains are cultivated in a defined medium as previously described for a sufficient time to reach a strain concentration between $5 \times 10^6$ and $5 \times 10^8$ cells/mL, advantageously between $10^7$ and $10^8$ cells/mL, and at least a second step wherein one or more carbon source enrichment solution(s) are added, simultaneously or successively, to the culture medium. Advantageously according to the invention, the carbon source enrichment solution can consist of a solution comprising a carbon source identical to or different from the carbon source used in the first step.

According to the invention, the sufficient time to reach a strain concentration between $5 \times 10^6$ and $5 \times 10^8$ cells/mL, advantageously between $10^7$ and $10^6$ cells/mL, can be between 24 h and 168 h, advantageously between 24 h and 96 h. However, the person skilled in the art will easily be able to determine the sufficient duration of time to reach a strain concentration between $5 \times 10^6$ and $5 \times 10^8$ cells/mL, by regularly analyzing the cell concentration in the culture medium. Any method for measuring the cell concentration in the culture medium can be used by the person skilled in the art to monitor the progress of the culture, such as, for example, cell counting using a Malassez chamber, or with a particle counter such as a Beckman®-brand "Z Coulter Counter®".

The purpose of the second step of the method according to the invention is to compensate for the consumption of the carbon source by the cells in culture during the first step.

According to a variant of the invention, the method can comprise a third step wherein one or more nitrogen source and/or phosphorus source and/or macroelement source, and/or microelement source, and/or vitamin source, advantageously nitrogen source and/or phosphorus source, enrichment solution(s) are added, simultaneously or successively, to the culture medium.

According to this variant of the invention, the purpose of this third step is to compensate for the consumption of the nitrogen, phosphorus, macroelement, microelement and/or vitamin sources by the cells in culture during the first steps.

According to another variant of the invention, steps 2 and 3 can be reversed.

According to still another variant of the invention, said method comprises only one second step wherein the enrichment solution can be a solution comprising at the same time the carbon source, the nitrogen source and the phosphorus source (a solution also called "C/N/P enrichment solution").

Indeed, the inventors were able to show that the addition to the second step of a solution comprising at the same time the carbon source, the nitrogen source and the phosphorus source, but whose molar concentration ratios of carbon/nitrogen/phosphorus atoms are perfectly defined, makes it possible to direct the metabolism of the strains in culture preferentially toward DHEA formation. The inventors showed, after having carried out numerous culture experiments and tests under various conditions, that this can be possible by creating a defined limitation of nitrogen and phosphorus.

DHEA production by the cells can increase if the additional substrate is added in the form of a nutrient solution with a defined molar ratio of carbon, nitrogen and phosphorus atoms wherein phosphorus is limited in relation to nitrogen and to carbon and wherein nitrogen is limited in relation to carbon.

Thus, according to the invention, the C/N/P-type enrichment solution can have for an equal quantity of carbon up two times more or two times less of nitrogen, and/or up to two times more or two times less of phosphorus in relation to the ratio 891:26:1.

Thus, the C/N/P-type enrichment solution can be used in the following molar ratios: 891:52:1, 891:26:1 and 891:13:1, 445:26:1, 445:13:1 and 445:6.5:1, 1782:104:1, 1782:52:1, and 1782:26:1.

Preferentially the C/N/P-type enrichment solution can have the following molar ratios: 891:26:1.

Obviously, the method according to the invention can comprise one or more repetitions of steps 2 and 3 irrespective of the order in which they were carried out initially.

The person skilled in the art can determine the quantity and the frequency of the additions according to the progress of the culture. At the beginning of culture, the elements present in the chemically defined medium, as previously described, make it possible to meet all the nutrient needs of the strains in culture. At the stage where the culture has reached a cell density between $5 \times 10^6$ and $5 \times 10^8$, even more precisely a cell density between $10^7$ and $10^8$ cells/mL, carbon substrates can be added. Moreover, according to the embodiment of the method, the additions of chemically defined nutrient solutions as previously described can be carried out when the culture reaches a cell density between $5 \times 10^6$ and $5 \times 10^8$, even more precisely a cell density between $10^7$ and $10^8$ cells/mL. These nutrient solutions can in particular constitute nitrogen or phosphorus sources.

According to the invention, the pH of the culture medium can be between 3 and 9, advantageously between 4 and 8.

Similarly, according to the invention, the culture temperature can be between 15 and 35° C., preferentially between 20 and 30° C.

According to the invention, the dissolved oxygen concentration can be adjusted between 4% and 40%, advantageously between 5% and 30%, during culture.

Of course, any other adjuvant necessary for culturing microalgae strains, particularly those concerned by the invention, well-known to the person skilled in the art, can be added according to the method according to the invention. For example, an antifoaming agent can be added during culture, for example 200 ppm Biospumex 153K®, available from Cognis, France.

The strains concerned by the invention can be cultivated according to the methods previously described, then recovered for any conceivable subsequent use. Preferentially, the strains concerned by the invention can be used to extract the lipid content therefrom, particularly DHEA. Methods of selective lipid extraction, including DHEA, are known to the person skilled in the art and, for example, are described in the article by Bligh, E. G. and Dyer, W. J. (1959) [A rapid method of total lipid extraction and purification, Can. J. Biochem. Physiol., 37:911-917].

The method according to the invention can make it possible to obtain a biomass the strains of which can thus have a DHEA productivity of at least 0.02 g/L/h, preferably at least 0.03 g/L/h, more preferentially at least 0.05 g/L/h, and more preferentially at least 0.1 g/L/h.

Similarly, the method according to the invention can make it possible to obtain a biomass the strains of which can have a DPA content in the fatty acids derived from the method of less than 3%, preferably less than 1%, more preferentially less than 0.5%, more preferentially still less than 0.1%, indeed than 0.01%.

The invention also relates to a method for producing DHEA, characterized in that the strains concerned by the invention are cultivated in a culture medium such as previously defined.

The biomass obtained by the method according to the invention can be subjected to any other known method able to lead to the separation of the oil contained in the strains.

For example, after fermentation, the biomass obtained can be concentrated, if necessary, to about 250 g/L. The purpose of this step is to concentrate the biomass of strains concerned by the invention in order to decrease the quantity of water to be evaporated during the following step. The biomass can be concentrated by centrifugation. The intensity of the artificial gravity applied can be greater than 4000 g. The biomass recovered in the centrifugation sediment can be concentrated, at a minimum, to 250 g/L. The effluents, consisting mainly of the culture medium, can be discarded.

The purpose of the drying step, which follows the concentration step, is to prepare the centrifugation sediment for a step of mechanical oil extraction. To that end, the drying step can consist in eliminating water to obtain dry matter that can have a relative moisture level between 3 and 5% (from 95 to 97% dry matter). This drying step can be carried out for example via cylinder drier technology or by other methods known to the person skilled in the art. The parameters for the drying step can be optimized according to the relative moisture content of the fermentation sludge. Furthermore, the drying parameters can also be optimized by correlating the temperature of the cylinders (controlling steam pressure above 3 bars) with the contact time of the sludge on the cylinders (cylinder rotation speed, 2 Hz).

The oil contained in the dry matter obtained by the preceding drying step can be extracted by all methods known to the person skilled in the art, for example by conventional extrusion-pressing technology. This mechanical extraction (pressing step) can generally be carried out by a press consisting of an endless screw applying pressure to a caged barrel closed by a nozzle. This device makes it possible to obtain a so-called "cold-pressed" oil or, if it is carried out with a heated-collar system, "hot-pressed" oil. In all cases, the mechanically recovered oil is never in contact with solvents. Mechanical pressing of the dry matter makes it possible to obtain a pigment-rich oil fraction and an oil cake consisting of between 3 and 5% residual oil. At this stage, it is possible to eliminate all lipids from the oil cake, and thus to recover all the oil produced during fermentation. The oil cake is then subjected to an additional solvent extraction step.

The pressed oil recovered from the pressing step can be clarified by conventional methods, such as centrifugation, to eliminate fine solid particles arising from the pressing of the biomass that are suspended in the oil (fines). A clarified oil is then obtained.

The fines can represent about 5% of the pressed oil obtained from the dry matter. The oil present in the fines can, just like the residual oil in the oil cake, be recovered by solvent extraction.

The clarified oil can be then processed, according to methods known to the person skilled in the art, into fatty acid ethyl esters by ethanol transesterification in basic medium. Thus, the fatty acids can be separated from the glycerol residue of the transesterification. The glycerol can then be eliminated by washing with water. The residual water present in the ethyl esters can generally be evaporated by vacuum distillation, for example using a Rotavapor®.

Once free of water, the fatty acid ethyl esters can be separated according to methods known to the person skilled in the art, for example, by molecular distillation. During this step, three fractions can, in general, be obtained:
  a light fraction, consisting of medium- and long-chain fatty acid ethyl esters (from capric acid ethyl ester or C10:0-EE to oleic acid ethyl ester or C18:1n9-EE),
  a heavy fraction, consisting of very long-chain ethyl esters (DHEA ethyl ester or DHA-EE);
  and, according to the culture method, a fraction consisting of concentrated pigments (α-carotene and β-carotene).

The DHA-EE can have a purity greater than 98% after the molecular distillation step.

The DHA-EE produced by the method of the invention can comprise less than 1%, even less than 0.5%, DPA n6. The DHA-EE can thus be used directly as a constituent in pharmaceutical compositions of therapeutic medicines.

The invention also relates to a biomass of microalgae having a gene encoding the small subunit 18s ribosomal RNA having a genetic similarity of at least 96% with the same gene of the strain of the species *Crypthecodinium cohnii* deposited in the CCAP (Culture Collection of Algae and Protozoa) under number CCAP 1104/3 able to be obtained by the method according to the invention, characterized in that it has a density at least greater than 50 g/L, preferably than 100 g/L, 150 g/L, 200 g/L or 250 g/L, more preferentially 270 g/L dry matter, said biomass further having a DHEA level at least greater than 5 g/L or 10 g/L, preferably greater than 20 g/L, and more preferentially greater than 30 g/L and optionally a PUFA level lower than 1% of the total fatty acid content, preferentially lower than 0.8% of the total fatty acid content.

Other advantages and features of the invention will become clear upon reading the examples described below as well as the appended drawings wherein:

FIG. 1A presents the evolution of the quantity of dry matter produced during the test. FIG. 1B presents the lipid profile of the oil contained in CCAP strain 1104/3 at the end of culture.

FIG. 2A presents the evolution of the quantity of dry matter produced during the test. FIG. 2B presents the lipid profile of the oil contained in CCAP strain 1104/3 at the end of culture.

FIG. 3A presents the evolution of the quantity of dry matter produced during the test. FIG. 3B presents the lipid profile of the oil contained in CCAP strain 1104/3 at the end of culture.

FIG. 4A presents the evolution of the quantity of dry matter produced during the test. FIG. 4B presents the lipid profile of the oil contained in CCAP strain 1104/3 at the end of culture.

FIG. 5A presents the evolution of the quantity of dry matter produced during the test. FIG. 5B presents the lipid profile of the oil contained in CCAP strain 1104/3 at the end of culture.

EXAMPLES

Example 1: Culture of a Strain of the Species *Crypthecodinium cohnii* (CCAP Strain 1104/3) According to the Method of the Invention in Chemically Defined Medium According to the Invention with the Addition of a Carbon Source Enrichment Solution

*Crypthecodinium cohnii* (CCAP strain 1104/3) cultures were prepared in 1 to 5 L fermentors (bioreactors) used with dedicated computer-controlled automated systems. The system was adjusted in pH by adding acid ($H_2SO_4$). The culture temperature was set to 28° C. Agitation was provided by 2 agitator impellers, Rushton and HTPG4. The dissolved oxygen pressure was regulated in the medium throughout the culture, by agitation speed (200-800 rpm), air flow rate (0.6-1.6 vvm) and oxygen flow rate (0-1.6 vvm). The regulation parameters, integrated in the automated control system, made it possible to maintain a $pO_2$ between 25% and 35%.

The total biomass concentration was monitored by measuring the dry mass (filtration on a Whatman GF/F filter then drying in a 105° C. oven for a minimum of 24 h before weighing).

The analyses of total lipids and FAME contents were carried out according to the methods classically described in the literature [Folch J. et al., A simple method for the isolation and purification of total lipids from animal tissues. J Biol Chem. 1957 May; 226(1):497-509].

The culture is prepared in the defined medium according to the invention, the composition of which is given in Table 2 below.

TABLE 2

|  | Ingredient | Concentration in g/L |
|---|---|---|
| Macroelements | NaCl | 5 |
|  | $MgCl_2\ 6H_2O$ | 1 |
|  | $N_aHCO_3$ | 0.19 |
|  | $K_2HPO_4$ | 0.5 |
|  | $CaCl_2\ 2H_2O$ | 1.9 |
|  | $FeCl_3\ 6H_2O$ | 0.02 |
|  | $H_3BO_3$ | 0.06 |
|  | $KNO_3$ | 2.4 |
| Microelements | $Na_2EDTA$ | 0.03 |
|  | $MnCl_2\ 4H_2O$ | 0.0045 |
|  | $ZnCl_2$ | 0.0003 |
|  | $CoCl_2\ 6H_2O$ | 0.00015 |
|  | $CuSO_4\ 5H_2O$ | 0.0018 |
|  | $NiSO_4\ 6H_2O$ | 0.0014 |
| Vitamins | Biotin | 0.000015 |
|  | Thiamin | 0.008 |
|  | Cobalamin | 0.00013 |
|  | Pantothenate | 0.0027 |
| Carbon source | Glycerol | 30 |

This chemically defined medium establishes a "1×" reference concentration for each of its components.

An organic carbon source enrichment solution, consisting of 712.3 g/L glycerol, makes it possible to feed the medium when the glycerol concentration measured in the fermentor drops below the 10 g/L threshold. This makes it possible to maintain the glycerol concentration between 10 g/L and 60 g/L, more preferentially between 20 g/L and 50 g/L.

A control culture is prepared in rich medium composed of 8.7 g/L yeast extract, 0.75 g/L $KNO_3$, 5 g/L sea salts and 30 g/L glycerol. A first enrichment solution for the control culture is composed of concentrated $KNO_3$ and yeast extract. These additions make it possible to increase the initially provided 1× quantity of $KNO_3$ and yeast extract to a 3× quantity. An organic carbon source enrichment solution, consisting of 712.3 g/L glycerol, makes it possible to feed the medium when the glycerol concentration measured in the fermentor drops below the 10 g/L threshold. This makes it possible to maintain the glycerol concentration between 10 g/L and 60 g/L, more preferentially between 20 g/L and 50 g/L.

Figure 1:
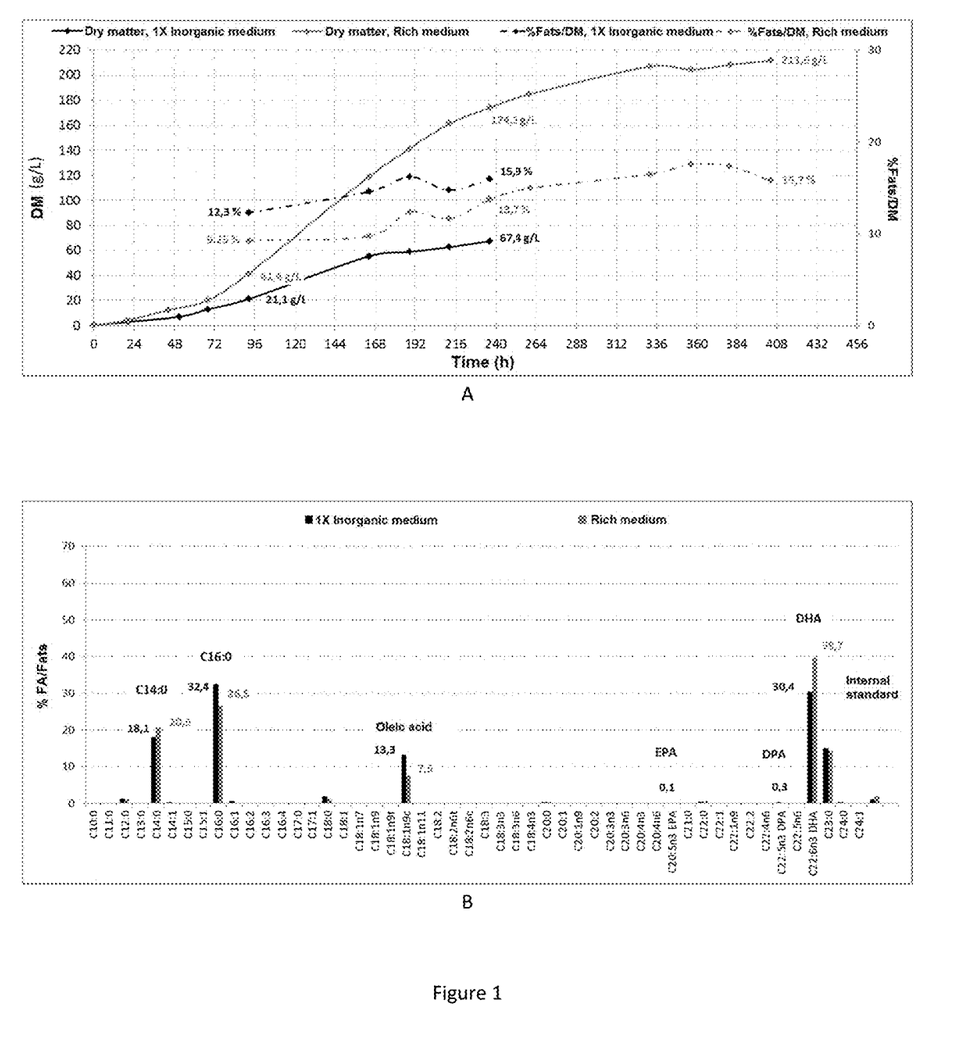
FIG. 1 presents the results obtained during culture of a strain of the species *Crypthecodinium cohnii* (CCAP strain 1104/3) according to the method of the invention in chemically defined medium according to the invention with the addition of a carbon source enrichment solution, compared to a culture in rich medium (Example 1).

FIG. 1 presents the results obtained during this test.

FIG. 1A presents the evolution of the quantity of dry matter produced during the test as well as the quantity of fats produced based on the quantity of dry matter produced (% Fats/DM) as a function of time in the medium according to the invention (1× inorganic medium) compared to culture in rich medium.

In terms of biomass, 67.4 g/L is obtained with the medium according to the invention (compared to 174.3 g/L with rich medium) after 236 h of culture, with about 15.9% fat content (compared to 13.7% with rich medium).

FIG. 1B presents the lipid profile of the oil contained in CCAP strain 1104/3 at the end of culture. It is noted in particular that PUFAs other than DHEA are at trace levels (<1%, preferentially <0.8%).

Moreover, the DHEA content in the fats rises to 30.4%, compared to 39.7% in the rich medium.

Thus, the growth of the strain on the medium of the invention makes it possible to reach high cell densities, greater than 50 g/L biomass, with the addition of a carbon source enrichment solution, but does not make it possible to equal the performance obtained on the control rich medium.

Figure 2:
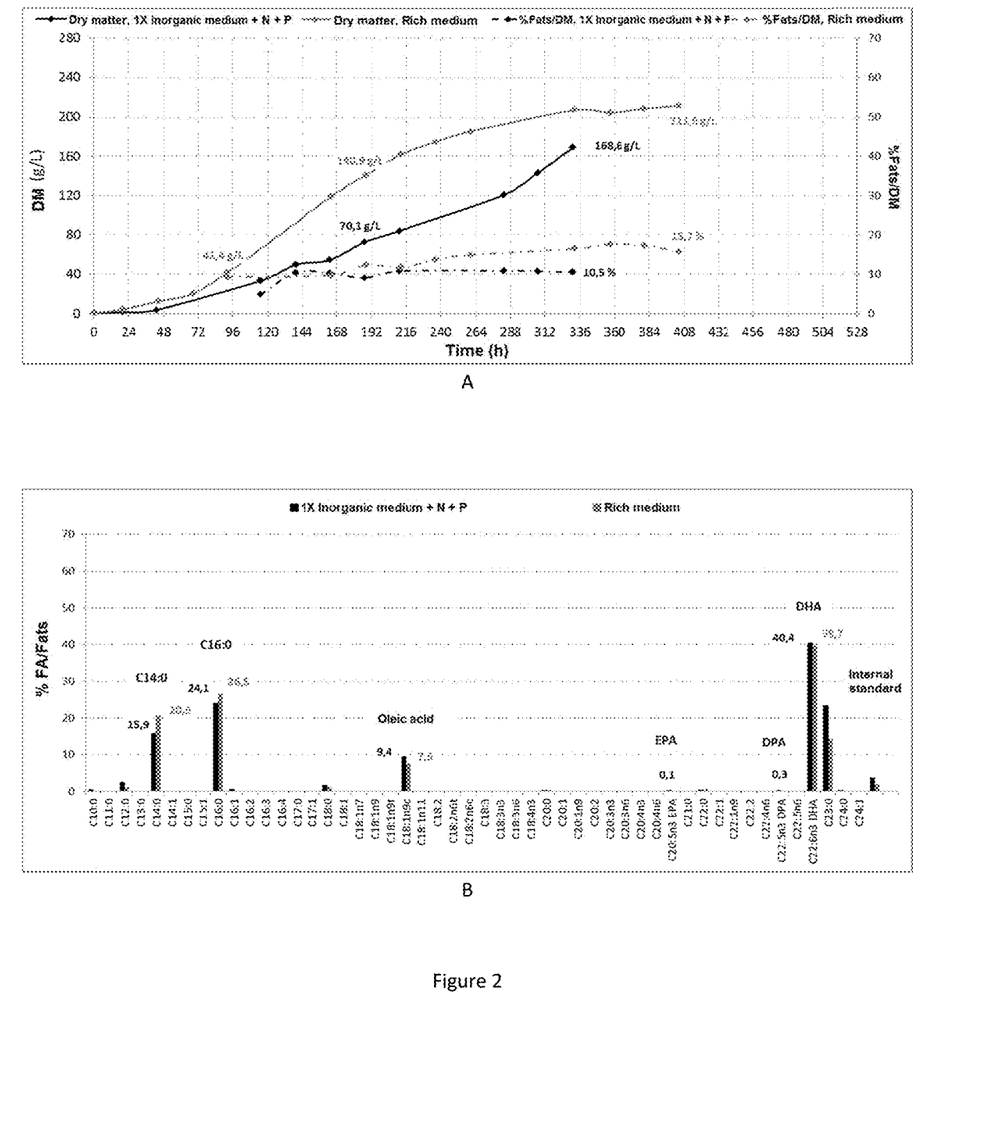
FIG. 2 presents the results obtained during culture of a strain of the species *Crypthecodinium cohnii* (CCAP strain 1104/3) according to the method of the invention in chemically defined medium according to the invention with the addition of a carbon source enrichment solution and a nitrogen and phosphorus source enrichment solution compared to culture in rich medium (Example 2).

Example 2: Culture of a Strain of the Species Crypthecodinium cohnii (CCAP Strain 1104/3) According to the Method of the Invention in Defined Medium According to the Invention with the Addition of a Carbon Source Enrichment Solution and a Nitrogen and Phosphorus Source Enrichment Solution The results of this example are illustrated in FIG. 2.

Crypthecodinium (CCAP strain 1104/3) cultures were prepared in fermentors, in a manner similar to that described in Example 1, but with the additional supply of a mineral enrichment solution consisting of $KNO_3$ at a concentration of 64.0 g/L and $K_2HPO_4$ at a concentration of 4.3 g/L, which makes it possible to increase the initial quantities of nitrogen and phosphorus and makes it possible to maintain productivity and thus to continue growth. The additions of this mineral enrichment solution are carried out once the culture reaches a cell density of $3 \times 10^7$ cells/mL, or after 92 h of culture.

A control culture is prepared in complex medium, as described in Example 1.

Under the conditions of this example, the cell density and the lipid content of the cells are close to those obtained in complex medium, after 330 h of culture (FIG. 2A).

In terms of biomass, 168.6 g/L is obtained with the medium according to the invention (compared to 210 g/L with rich medium), with about 10% fats.

FIG. 2B presents the lipid profile of the oil contained in CCAP strain 1104/3 at the end of culture. It is noted in particular that PUFAs other than DHEA are at trace levels (<1%, preferentially <0.8%). Moreover, the quantity of DHEA is equivalent to the profile obtained in complex medium, with 40.4% compared to 39.7% DHEA in rich medium.

Thus, the growth of the strain on the medium of the invention, with the addition of a carbon source enrichment solution coupled with the addition of a nitrogen and phosphorus source enrichment solution, makes it possible to reach high cell densities close to those obtained on the control rich medium, and makes it possible to obtain a DHEA content in the fats identical to that of the control rich medium.

Figure 3:
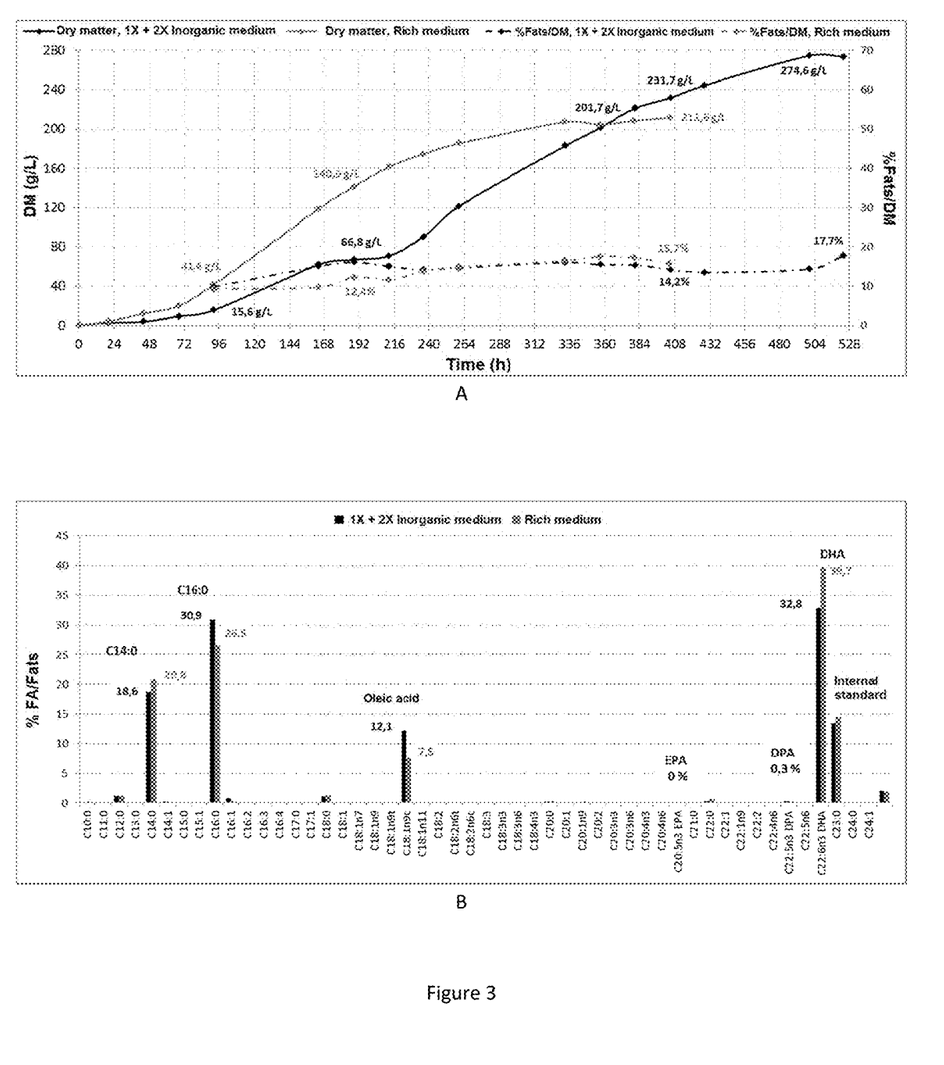
FIG. 3 presents the results obtained during culture of a strain of the species *Crypthecodinium cohnii* (CCAP strain 1104/3) according to the method of the invention in chemically defined medium according to the invention with the addition of a carbon source enrichment solution and a macroelement, in particular containing nitrogen and phosphorus, microelement and vitamin enrichment solution, which makes it possible to supply the equivalent of twice the quantity of elements present in the defined medium used initially for a total mineral and vitamin supply corresponding to three times the initial quantity ("3x" total) after the additions, compared to culture in rich medium (Example 3).

Example 3: Culture of a Strain of the Species Crypthecodinium cohnii (CCAP Strain 1104/3) According to the Method of the Invention in Defined Medium According to the Invention with the Addition of a Carbon Source Enrichment Solution and a Macroelement, in Particular Containing Nitrogen and Phosphorus, Microelement and Vitamin Enrichment Solution The results of this example are illustrated in FIG. 3.

Crypthecodinium (CCAP strain 1104/3) cultures were prepared in fermentors, in a manner similar to that described in Example 2, but with a modification of the mineral enrichment solution.

In this example, the mineral enrichment solution is composed of all the minerals and vitamins present in the initial culture medium. The addition makes it possible to supply the equivalent of twice the quantity of minerals and vitamins present in the initial culture medium, for a total mineral and vitamin supply corresponding to three times the initial quantity ("3×" total) after the additions.

A control culture is prepared in complex medium, as described in Example 1.

The progressive supply of minerals and vitamins makes it possible to reach up to 274.6 g/L dry matter consisting of 18% fats with a DHEA content of 32.6% (see FIGS. 3A and B).

Thus, the conditions of Example 3 make it possible to exceed the performance obtained on the rich medium and the inorganic medium of Example 2.

FIG. 3B shows the lipid profile of the oil contained in CCAP strain 1104/3 at the end of culture. It is noted in particular that PUFAs other than DHEA are at trace levels (<1%, preferentially <0.8%).

Moreover, the DHEA content in the fats rises to 32.8% compared to 39.7% in the rich medium.

Thus, the growth of the strain on the medium of the invention, with the addition of a carbon source enrichment solution coupled with the addition of a macroelement, in particular containing nitrogen and phosphorus, microelement and vitamin enrichment solution, makes it possible to reach high cell densities greater than those obtained on the control rich medium, and makes it possible to obtain a DHEA content in the fats close to that of the control rich medium.

Figure 4:
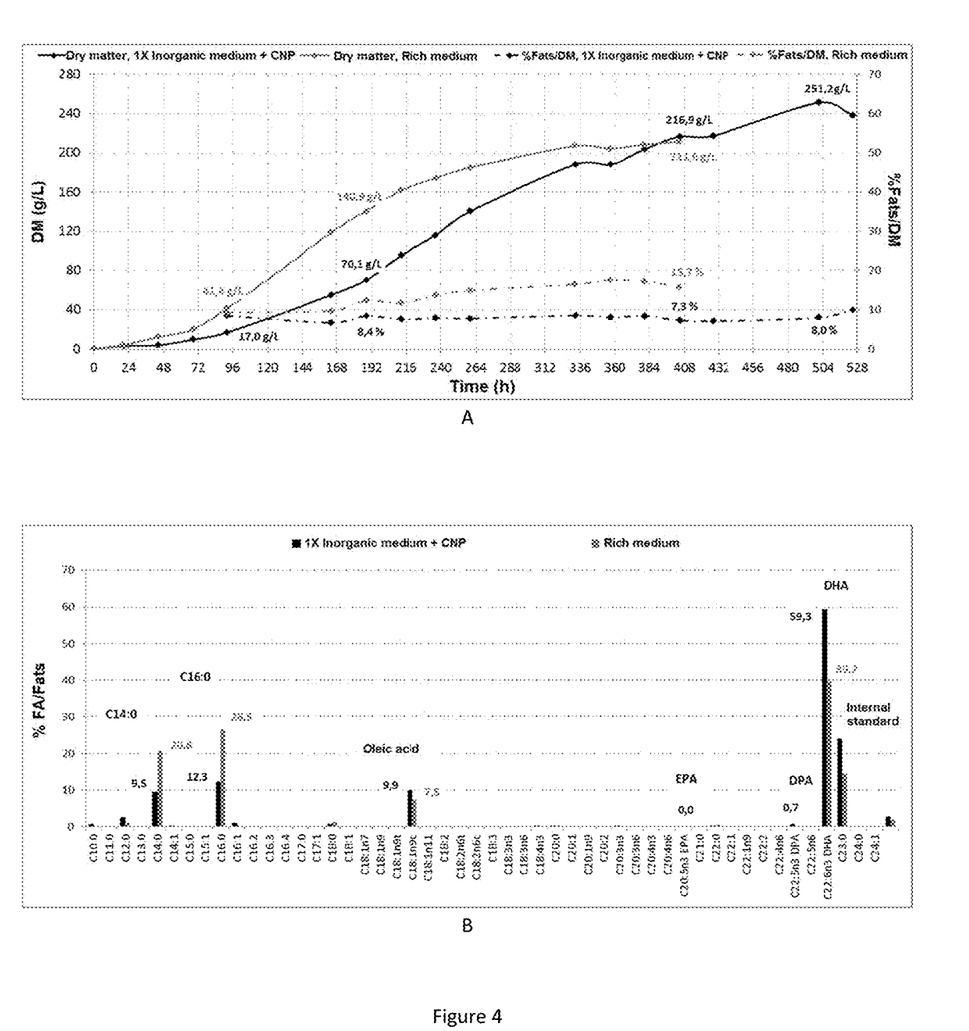
FIG. 4 presents the results obtained during culture of a strain of the species *Crypthecodinium cohnii* (CCAP strain 1104/3) according to the method of the invention in chemically defined medium according to the invention with the addition of a C/N/P-type enrichment solution, compared to culture in rich medium (Example 4).

Example 4: Culture of a Strain of the Species Crypthecodinium cohnii (CCAP Strain 1104/3) According to the Method of the Invention in Defined Medium According to the Invention with the Addition of a C/N/P-Type Enrichment Solution The results of this example are illustrated in FIG. 4.

Crypthecodinium (CCAP strain 1104/3) cultures were prepared in fermentors, in a manner similar to that described in Example 2.

The procedure was modified in terms of the nature of the enrichment solutions. In this example, the additional substrate is added in the form of additions of a solution called "C/N/P nutrient solution". The nutrient solution consists of a carbon substrate (glycerol), an inorganic nitrogen source ($KNO_3$) and an inorganic phosphorus source ($K_2HPO_4$). This nutrient solution has a defined molar ratio of carbon, nitrogen and phosphorus atoms: 891:26:1. This ratio was adjusted by the inventors to create a defined limitation of nitrogen and phosphorus, and thus to preferentially direct the metabolism toward DHEA production.

A control culture is prepared in rich medium as described in Example 1.

The addition of a C/N/P solution in a molar ratio of 891:26:1 makes it possible to reach 251.2 g/L dry matter consisting of 8% fats with a 59.3% DHEA content (FIGS. 4A and B).

Thus, according to this embodiment of the invention, the supply of carbon, nitrogen and phosphorus sources during culture in a chemically defined medium makes it possible to increase the DHEA content in the fats up to a value of 59.3%. This performance exceeds all those described in the prior art, whether in inorganic medium or in rich medium. This performance also makes it possible to improve the methods described in Examples 1, 2 and 3.

FIG. 4B shows the lipid profile of the oil contained in CCAP strain 1104/3 at the end of culture. It is noted in particular that PUFAs other than DHEA are at trace levels (<1%, preferentially <0.8%).

Moreover, the DHEA content in the fats rises to 59.3%, compared to 39.7% DHEA in rich medium.

Thus, compared to Examples 1, 2 and 3, the controlled supply of carbon, nitrogen and phosphorus source (C/N/P-type enrichment solution in a molar ratio of 891:26:1) makes it possible to significantly enrich the oil in DHEA, while maintaining high densities and productivities.

Conclusions Upon Reading the Results of the Examples

Microalgae strains concerned by the invention cultivated according to the invention make it possible to produce significant quantities of biomass, containing lipids that are rich in DHEA and low in DPA.

Indeed, the method of the invention in heterotrophic or mixotrophic conditions makes it possible to obtain a biomass concentration at least equal to if not greater than 50 g/L matter dry and may reach up to more than 250 g/L dry matter. This dry matter can consist of more than 10% fats, this content potentially going up to 60% lipids (FIG. 3A) with a DHEA content of up to more than 59% (FIG. 4B).

Generally, the quantity of DHEA obtained with the method of the invention is at least as great as that obtained using rich culture media as described in the prior art. For example, the results of Example 2 show that 40.4% DHEA is obtained with culture in defined medium according to the invention (Table 1) in a bioreactor and that 39.7% DHEA is obtained for the control culture (complex medium).

Other unwanted PUFAs, particularly DPA, generally represent less than 3%, and up to less than 0.01% of the fatty acids.

Generally, according to the method of the invention, PUFAs other than DHEA are at trace levels (<1%, preferentially <0.8%).

Example 5: Culture of a Strain of the Species *Crypthecodinium cohnii* (CCAP Strain 1104/3) According to the Method of the Invention in Defined Medium According to the Invention with the Addition of a Macroelement, in Particular Containing Nitrogen and Phosphorus, Microelement and Vitamin Enrichment Solution and the Addition of a C/N/P-Type Enrichment Solution The culture was prepared in conditions similar to that of Example 1.

The culture is prepared in the defined medium according to the invention, the composition of which is given in Table 3 below.

TABLE 3

| | Compound | Concentration (g/L) |
|---|---|---|
| Macroelement solution | NaCl | 4 |
| | $MgCl_2\ 6H_2O$ | 0.97 |
| | $NaHCO_3$ | 0.19 |
| | $KNO_3$ | 3.69 |
| | $K_2HPO_4$ | 0.5 |
| | $CaCl_2\ 2H_2O$ | 1.9 |
| | $FeCl_3\ 6H_2O$ | 0.02 |
| | $H_3BO_3$ | 0.06 |
| Microelement solution | $Na_2EDTA$ | 0 |
| | $MnCl_2\ 4H_2O$ | 0.009 |
| | $ZnCl_2$ | 0.0006 |
| | $CoCl_2\ 6H_2O$ | 0.0003 |
| | $CuSO_4\ 5H_2O$ | 0.000034 |
| | $NiSO_4\ 6H_2O$ | 0.00033 |
| Vitamin solution | Biotin | 0.0000075 |
| | Thiamin | 0.004 |
| | Vitamin B12 | 0.00006 |
| | Pantothenate | 0.0014 |
| Carbon source | Glycerol | 20 |

In this example, a mineral enrichment solution consisting of all the minerals and vitamins present in the initial culture medium other than $KNO_3$ and $KH_2PO_4$ is used to enrich the medium for a total mineral and vitamin supply corresponding to three times the initial quantity ("3×" total) after the additions. Moreover, the additional substrate is added in the form of additions of a solution called "C/N/P nutrient solution". The nutrient solution consists of a carbon substrate (glycerol), an inorganic nitrogen source (KNO3) and an inorganic phosphorus source (K2HPO4). This nutrient solution has a defined molar ratio of carbon, nitrogen and phosphorus atoms: 445:13:1. This ratio was adjusted to create a defined limitation of nitrogen and phosphorus, and thus to preferentially direct the metabolism toward DHEA production while maintaining the biomass in a state allowing sufficient catalytic activity to maintain good productivity.

A control culture is prepared in rich medium as described in Example 1.

Figure 5:
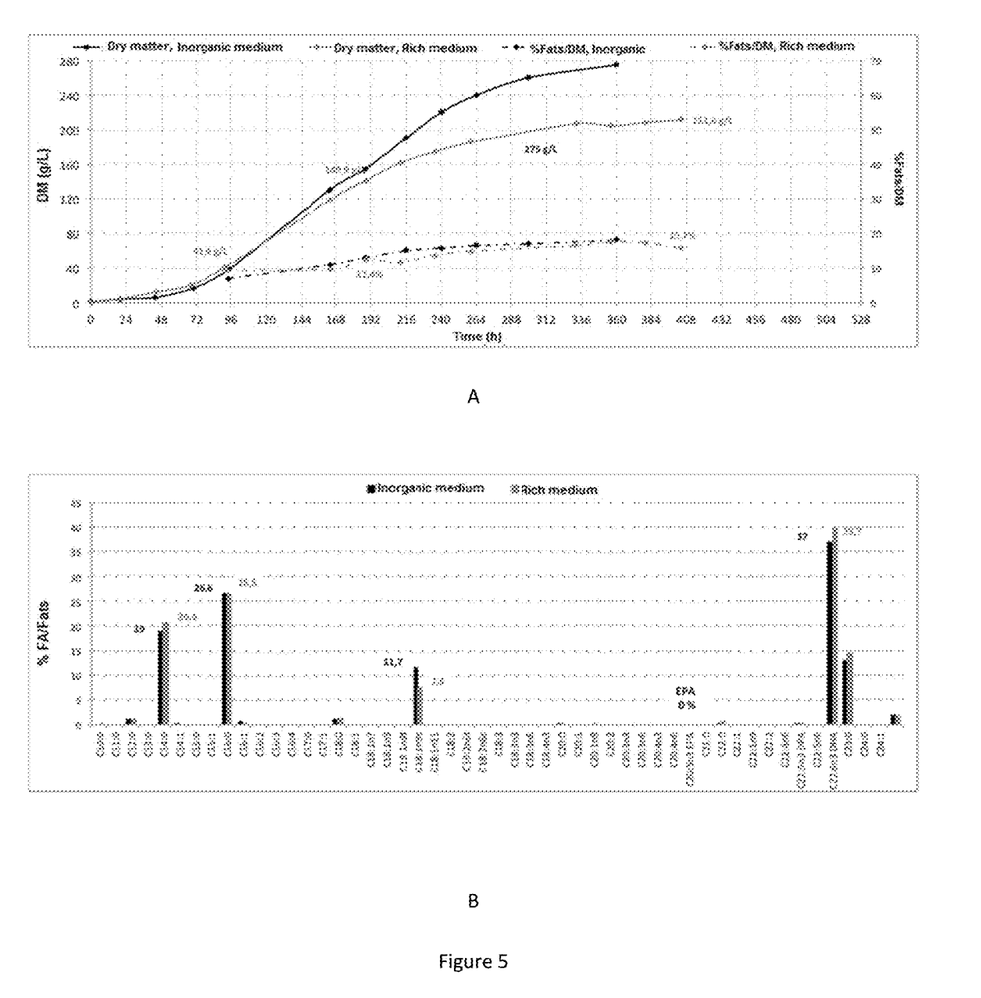
FIG. 5 presents the results obtained during culture of a strain of the species *Crypthecodinium cohnii* (CCAP strain 1104/3) according to the method of the invention in defined medium according to the invention with the addition of a macroelement, in particular containing nitrogen and phosphorus, microelement and vitamin enrichment solution and the addition of a C/N/P-type enrichment solution (Example 5).

The addition of the mineral and vitamin enrichment solution and the C/N/P solution in a molar ratio of 445:13:1 makes it possible to reach 275 g/L dry matter consisting of 18% fats with a 37% DHEA content (FIGS. 5A and B).

Thus, according to this embodiment of the invention, supplying minerals and vitamins on the one hand, and carbon, nitrogen and phosphorus sources on the other, during culture in a chemically defined medium, makes it possible to obtain satisfactory performance in terms of fatty acid accumulation and DHEA content while obtaining good productivity.

FIG. 5B shows the lipid profile of the oil contained in CCAP strain 1104/3 at the end of culture. It is noted in particular that PUFAs other than DHEA are at trace levels (<1%).

The invention claimed is:

1. Method for producing a biomass of microalgae comprising the steps of a) culturing the microalgae in a culture medium and b) harvesting the biomass from the culture medium, wherein step a) of culturing the microalgae comprises at least a first step a1) wherein said microalgae are cultivated in a chemically defined medium, comprising
macroelements comprising a mixture of sodium chloride (NaCl), magnesium chloride, sodium bicarbonate ($N_aHCO_3$), potassium hydrogen phosphate ($K_2HPO_4$), calcium chloride, iron (III) chloride ($FeCl_36H_2O$), boric acid ($H_3BO_3$) and a nitrogen source;

microelements comprising a mixture of disodium ethylenediaminetetraacetic acid ($Na_2EDTA$), manganese (II) chloride tetrahydrate ($MnCl_2 4H_2O$), zinc chloride ($ZnCl_2$), cobalt chloride hexahydrate ($CoCl_2 6H_2O$), copper sulfate pentahydrate ($CuSO_4 5H_2O$), and nickel sulfate hexahydrate ($NiSO_4 6H_2O$);

vitamins comprising a mixture of biotin, thiamin, vitamin B12, and vitamin B5;

and a carbon source;

for a sufficient time to reach a strain concentration between $5 \times 10^6$ and $5 \times 10^8$ cells/mL, and at least a second step a2) wherein one or more carbon source enrichment solution(s) are added, simultaneously or successively, to the culture medium, wherein the microalgae is a microalgae strain having a gene encoding the small subunit 18s ribosomal RNA having a genetic similarity of at least 96% with the same gene of the strain of the species *Crypthecodinium cohnii* deposited in the CCAP (Culture Collection of Algae and Protozoa) under number CCAP 1104/3, and wherein the biomass is cultured at a density at least greater than 150 g/L dry matter.

2. Method according to claim 1, wherein in the chemically defined medium of step a1), sodium chloride is at a concentration between 2 and 8 g/L, magnesium chloride is at a concentration between 0.6 and 1.4 g/L, sodium bicarbonate is at a concentration between 0.14 and 0.26 g/L, the nitrogen source is at a concentration between 1.7 and 3.1 g/L, potassium hydrogen phosphate is at a concentration between 0.3 and 0.7 g/L, calcium chloride is at a concentration between 1.4 and 2.6 g/L, iron (III) chloride is at a concentration between 0.016 and 0.024 g/L, boric acid is at a concentration between 0.046 and 0.74 g/L, disodium ethylenediaminetetraacetic acid is at a concentration between 0 and 0.08 g/L, manganese (II) chloride tetrahydrate is at a concentration between 0.001 and 0.02 g/L, zinc chloride is at a concentration between 0.0001 and 0.0008 g/L, cobalt chloride hexahydrate is at a concentration between 0.00005 and 0.0005 g/L, copper sulfate pentahydrate is at a concentration between 0.00007 and 0.004 g/L, nickel sulfate hexahydrate is at a concentration between 0.0005 and 0.003 g/L, biotin is at a concentration between $0.5 \times 16^{-6}$ and $1.5 \times 10^{-4}$ g/L, thiamin is at a concentration between $0.5 \times 16^{-6}$ and $1.5 \times 10^{-4}$ g/L, cobalamin is at a concentration between $0.5 \times 16^{-6}$ and $1.5 \times 10^{-4}$ g/L and pantothenate is at a concentration between $0.5 \times 16^{-6}$ and $1.5 \times 10^{-4}$ g/L.

3. Method according to claim 1, wherein in the chemically defined medium of step a1), sodium chloride is at a concentration between 4 and 6 g/L, magnesium chloride is at a concentration between 0.8 and 1.2 g/L, sodium bicarbonate is at a concentration between 0.16 and 0.24 g/L, the nitrogen source is at a concentration between 1.9 and 2.9 g/L, potassium hydrogen phosphate is at a concentration between 0.4 and 0.6 g/L, calcium chloride is at a concentration between 1.6 and 2.4 g/L, iron (III) chloride is at a concentration between 0.018 and 0.022 g/L, boric acid is at a concentration between 0.048 and 0.72 g/L, disodium ethylenediaminetetraacetic acid is at a concentration between 0.015 and 0.06 g/L, manganese (II) chloride tetrahydrate is at a concentration between 0.002 and 0.01 g/L, zinc chloride is at a concentration between 0.00015 and 0.0006 g/L, cobalt chloride hexahydrate is at a concentration between 0.00007 and 0.0003 g/L, copper sulfate pentahydrate is at a concentration between 0.0009 and 0.0036 g/L, nickel sulfate hexahydrate is at a concentration between 0.0007 and 0.0028 g/L, biotin is at a concentration between $1 \times 10^{-6}$ and $1 \times 10^{-4}$ g/L, thiamin is at a concentration between $1 \times 10^{-6}$ and $1 \times 10^{-4}$ g/L, cobalamin is at a concentration between $1 \times 10^{-6}$ and $1 \times 10^{-4}$ g/L and pantothenate is at a concentration between $1 \times 10^{-6}$ and $1 \times 10^{-4}$ g/L.

4. Method according to claim 1, wherein the nitrogen source is selected among the group consisting in a nitrate salt, a glutamate salt, an ammonium salt and urea.

5. Method according to claim 1, wherein the carbon source is selected among the group consisting in one (or more) carbohydrate(s), one (or more) acetate(s), one or more alcohols, one or more complex molecules and mixtures thereof.

6. Method according to claim 1, wherein in the first step a1) the carbon source is at a concentration between 10 mM and 500 mM.

7. Method according to claim 1, wherein culture is in heterotrophic or mixotrophic conditions.

8. Method according to claim 1, wherein step a) of culturing the microalgae comprises a third step a3) wherein one or more nitrogen source and/or phosphorus source and/or macroelement source, and/or microelement source, and/or vitamin source, enrichment solution(s) are added, simultaneously or successively, to the culture medium.

9. Method according to claim 1, wherein in the second step a2) the enrichment solution is a solution comprising at the same time the carbon source, the nitrogen source and the phosphorus source (a solution also called "C/N/P enrichment solution").

10. Method according to claim 9, wherein the C/N/P enrichment solution has the ratio 891:26:1 for C/N/P or has, for a fixed quantity of carbon, up to two times more or two times less nitrogen than this ratio, and/or up to two times more or two times less phosphorus than this ratio.

11. Method according to claim 10, wherein the ratio of C/N/P in the enrichment solution are selected from the group consisting in: 891:52:1, 891:26:1, 891:13:1, 445:26:1, 445:13:1, 445:6.5:1, 1782:104:1, 1782:52:1, and 1782:26:1.

12. Method according to claim 1, wherein in the chemically defined medium of step a1), sodium chloride is at a concentration of 5 g/L, magnesium chloride is at a concentration of 1 g/L, sodium bicarbonate is at a concentration of 0.19 g/L, the nitrogen source ($KNO_3$) is at a concentration of 2.4 g/L, potassium hydrogen phosphate is at a concentration of 0.5 g/L, calcium chloride is at a concentration of 1.9 g/L, iron (III) chloride is at a concentration of 0.02 g/L, boric acid is at a concentration of 0.06 g/L, disodium ethylenediaminetetraacetic acid is at a concentration of 0.03 g/L, manganese (II) chloride tetrahydrate is at a concentration of 0.0045 g/L, zinc chloride is at a concentration of 0.0003 g/L, cobalt chloride hexahydrate is at a concentration of 0.00015 g/L, copper sulfate pentahydrate is at a concentration of 0.0018 g/L, nickel sulfate hexahydrate is at a concentration of 0.0014 g/L, biotin is at a concentration of 0.000015 g/L, thiamin is at a concentration of 0.008 g/L, cobalamin is at a concentration of 0.00013 g/L, pantothenate is at a concentration of 0.0027 g/L and the carbon source is at a concentration of 30.00 g/L.

13. Method according to claim 1, wherein it further comprises downstream steps of, of lipid extraction form the harvested biomass, and optionally of DHEA extraction from the lipids recovered.

14. Method according to claim 13, wherein it further comprises a step of purifying the DHEA produced in the form of DHEA esters.

15. Method according to claim 1, wherein the biomass is cultured at a density at least greater than 200 g/L dry matter.

16. Method according to claim 1, wherein the biomass is cultured at a density at least greater than 250 g/L dry matter.

17. Method according to claim 1, wherein the biomass is cultured at a density at least greater than 270 g/L dry matter.

18. Method according to claim 1, wherein the microalgae are cultured for an enrichment in their docosahexaenoic acid (DHEA) content.

19. Method according to claim 7, wherein the cultured microalgae have a DHEA level at least greater than 20 g/L.

20. Method according to claim 7, wherein the cultured microalgae have a DHEA level at least greater than 30 g/L.

21. Method according to claim 8, wherein the cultured microalgae have a level of PUFAs other than DHEA lower than 1% of the total fatty acid content.

22. Method according to claim 8, wherein the cultured microalgae have a level of PUFAs other than DHEA lower than 0.8% of the total fatty acid content.

\* \* \* \* \*